United States Patent [19]

Tebbe

[11] 3,933,876
[45] Jan. 20, 1976

[54] HYDRIDE COMPLEXES OF METALS OF GROUPS IVB AND VB

[75] Inventor: Frederick Nye Tebbe, Hockessin, Del.

[73] Assignee: E. I. Du Pont de Nemours and Company, Wilmington, Del.

[22] Filed: July 2, 1974

[21] Appl. No.: 485,317

Related U.S. Application Data

[63] Continuation-in-part of Ser. No. 191,902, Oct. 22, 1971, abandoned.

[52] U.S. Cl............. 260/429 R; 75/118; 117/35 R; 117/107.2 R; 117/123 B; 117/124 T; 117/124 C; 260/429.3; 260/429.5; 260/677 H; 260/683.15 D
[51] Int. Cl.². ....................... C07F 7/00; C07F 7/28
[58] Field of Search........... 260/429 R, 429.3, 429.5

[56] References Cited
UNITED STATES PATENTS

3,695,853   10/1972   Klanberg.................... 260/429 R X

OTHER PUBLICATIONS

Carlin, Transition Metal Chemistry, V. 1, pp. 116, 121–141
Lippard, Progress in Inorganic Chem., Vol. 16, pp. 81 and 91, (1972).

*Primary Examiner*—Helen M. Sneed

[57] ABSTRACT

Disclosed herein are complex transition metal hydrides of the formula

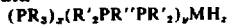

wherein:
- M is Nb, Ta, Ti, Zr, or Hf
- R is alkyl or aryl of up to 8 carbon atoms
- R' is alkyl or aryl of up to 8 carbon atoms
- R" is alkylene of up to 3 carbon atoms, or o-phenylene with the provisos that:
when
  M is Nb or Ta,
  $x=0, 1, 2$ or $4$; $y=0, 2$ or $3$; $z=1, 3$ or $5$; and $2x=4y+z=13$ and
when M is Ti, Zr or Hf,
  $x=0, y=1$, and $z=3$.

Also taught is a process for making these hydrides.

22 Claims, No Drawings

HYDRIDE COMPLEXES OF METALS OF GROUPS IVB AND VB

CROSS-REFERENCE TO RELATED APPLICATION

This is a continuation-in-part of my copending application Ser. No. 191,902, filed Oct. 22, 1971, now abandoned.

BACKGROUND OF THE INVENTION

1. Field of the Invention

This invention concerns hydride coordination complexes of transition metals of Groups IVB and VB, containing tertiary phosphines.

2. Description of the Prior Art

Heretofore, successful attempts to isolate hydride complexes of Group IVB metals, Nb and Ta, have been made by invoking the added stabilizing ability of special $\pi$-bonded ligands such as $\pi$-cyclopentadienyl. The very stability of the metal-cyclopentadienyl bond, however, prevents such groups from labile inter-conversion with hydride or other ligands. Thus, as shown by Marvich and Brintzinger, J. Am. Chem. Soc., 93, 2046 (1971) for Ti and by Barefield, Parshall and Tebbe, ibid., 92, 5234 (1970) for Nb and Ta, the cyclopentadienyl ligands cannot be reversibly replaced by multiple hydride ligands or other coordinating groups.

The novel hydrides of this invention contain ligands that are sufficiently stable for isolation and yet sufficiently labile to afford ready replacement by reacting species during use, say, in promoting hydrogen transfer reactions. The novel hydrides are soluble in organic media and thus are particularly desirable to facilitate homogeneous hydrogen transfer reactions.

SUMMARY OF THE INVENTION

The novel products of this invention are hydrides of the formula $(PR_3)_x(R_2'PR''PR_2')_yMH_z$ wherein:
M is Nb, Ta, Ti, Zr, or Hf
R is alkyl or aryl of up to 8 carbon atoms
R' is alkyl or aryl of up to 8 carbon atoms
R'' is alkylene of up to 3 carbon atoms, or o-phenylene with the provisos that:
when
M is Nb or Ta,
$x = 0, 1, 2$ or $4$; $y = 0, 2$ or $3$; $z = 1, 3$ or $5$; and $2x + 4y + z = 13$; and
when
M is Ti, Zr or Hf, $x = 0$, $y = 1$, and $z = 3$.

Also taught herein is the novel process for making the hydride complexes, comprising reacting a metal-source compound selected from metal alkyls, aryls and halides with a tertiary phosphine in the presence of a source of hydrogen.

The terms alkyl and aryl used here and in the claims are meant to include those mixed aralkyl and alkaryl groups such as $C_6H_5CH_2-$ and $CH_3CH_6H_4-$.

DETAILS OF THE INVENTION

The neutral ligands $PR_3$ may contain alkyl or aryl substituents as R groups. The size of the alkyl or aryl groups attached to phosphorus is limited to 8 carbon atoms to avoid the undesired effects that extremely large of bulky groups may have on the stability or solubility of the complexes. The three alkyl or aryl groups attached to any one P atom may be the same or different, although it is most convenient to obtain tertiary ligands, $PR_3$, having three identical R groups. It is preferred to have methyl, ethyl or phenyl groups as the R substitutent.

The stabilizing effect of bidentate ligands capable of forming chelate complexes is well known. It is also known that 5-membered chelate rings are most stable and that 6- and 4-membered rings have smaller stabilizing effects. Those complex metal hydrides of the invention having at least one bidentate group $R_2'PR''PR_2'$ are preferred for stability; especially preferred are those where R'' is ethylene, $-CH_2CH_2-$, or o-phenylene group capable of forming a 5-membered chelate ring. Preferred values for R' are methyl and phenyl. Because of their stability and high hydridic H content, the especially preferred hydrides of the invention are $[(CH_3)_2P-CH_2-CH_2-P(CH_3)_2]_3NbH_5$ and $[(CH_3)_2P-CH_2-CH_2-P(CH_3)_2]_2TaH_5$ The complex hydrides of the group VB metals Nb and Ta are consistent with the "18-electron-rule." In these the number and type of bonds formed by the metal, M, is such as to simulate the 18 electron configuration of the next inert gas element. Such behavior is described by M. L. H. Green, "The Transition Elements", Vol. 2 of "organometallic Compounds", G. E. Coates, M. L. H. Green, and K. Wade, Editors, Methuen Co., Ltd., London 1968, p. 2.

In the novel complexes herein, the Nb and Ta each furnish the 5 electrons characteristic of this group; each coordinating element P donates a pair of electrons for each bond to the central metal M; and each hydrogen furnishes one electron. The number of electrons available for bonding to Nb or Ta are then 5 + 2 for each monodentate group +4 for each bidentate group + 1 for each hydrogen atom. Thus, conforming to the 18-electron-rule, Nb and Ta would form the entire series of complexes given by the formula $2x + 4y + z = 13$.

The Nb and Ta hydrides of this invention have the following values of x, y and z:

| x | y | z |
|---|---|---|
| 0 | 2 | 5 |
| 0 | 3 | 1 |
| 4 | 0 | 5 |
| 2 | 2 | 1 |
| 1 | 2 | 3 |

The stable hydrides of the group IVB transition metals, Ti, Zr, Hf, are limited to those of the formula:
$R_2'PR''PR_2'MH_3$.

An analysis of the infrared absorption due to the M-H bonds indicates that the hydridic hydrogens are bridged between group IVB metal atoms. This suggests that these hydride complexes are polymers of the empirical formula given above.

PROCESS

The novel products of the invention are made by reacting a metal source selected from the metal alkyls, the metal aryls and the metal halides with a tertiary phosphine in the presence of a hydrogenation source.

If a halide such as $TaCl_5$ is used as the metal source then an active source of hydrogen containing an alkali metal must be used in order to reduce the metal and remove the halogen. Examples of such an active hydrogenation source are potassium metal and hydrogen, sodium metal and hydrogen, or sodium hydride.

Preferred metal sources are the alkyl and aryl compounds of the metal, M. Especially preferred are the phenyl and benzyl compounds of the metals, exemplified by $(C_6H_5)_6Ta^-$ and $(C_6H_5CH_2)_4Zr$. The most generally applicable organometallic sources of the metal ion do not include unsaturated groups such as the allyl or cyclopentadienyl radicals which form stable $\pi$-bonded ligands, since these may only be partially replaced by the tertiary group VA ligands which characterize the hydrides of this invention. When the alkyl and aryl compounds are used as a metal source it is not necessary to use an alkali metal to provide a more active source of hydrogen and gaseous hydrogen can be used directly in the reaction liquid.

The desired tertiary phosphine can be directly added in excess to the reaction mixture if the complex is to contain identical group VA ligands. If mixed ligands are desired in the complex it will be understood that the more tightly bound ligands must not be present in such excess as to displace the less tightly bound ligands which are intended to be present. The order of stability described above (i.e. 5-membered >6-membered>4-membered>monodentate) will guide the order of addition and relative quantities of mixed ligands.

The reactions are generally carried out in an aprotic solvent in which the reactants and the products have some solubility. Ethers and particularly tetrahydrofuran (THF) constitute preferred media but aromatic hydrocarbons may also be used. When a liquid reagent such as $(CH_3)_2P-CH_2CH_2-P(CH_3)_2$ is used it may also serve as the reaction medium.

Reactions may be carried out at temperatures ranging from room temperature to about 140°C. The solution should be agitated during hydrogenation which can be carried out at pressures ranging from atmospheric to about 400 atmospheres. It is most convenient to carry out the reaction in a shaker vessel at about 100 atmospheres hydrogen pressure. The reaction is usually complete within a few hours but it is convenient to maintain the reaction mixture overnight.

When reaction is completed it is desirable to filter off any solid residue and recover the product by evaporation of the solvent or liquid reagents. The complex hydrides can be recrystallized from toluene or hexane. They react readily with air and water.

DESCRIPTION OF THE PREFERRED EMBODIMENTS

The following Examples are given to illustrate but not to limit the invention. Unless stated to the contrary, all procedures were carried out in an inert atmosphere of nitrogen or argon. Solvents were purged with nitrogen or argon and were purified of traces of moisture by conventional techniques. Temperatures are in degrees Centigrade and the abbreviation dmpe is used for bis(-dimethylphosphino)ethane, $(CH_3)_2PCH_2CH_2P(CH_3)_2$.

EXAMPLE 1

Preparation of $[(CH_3)_2PCH_2CH_2P(CH_3)_2]_2TaH_5$

Phenyllithium was prepared as follows:

To 14 g. (2 moles) of lithium ribbon suspended in 550 ml. of ether was added with stirring 157 g. (1 mole) of bromobenzene over a 1 hr. period. The mixture was further stirred for one-half hr. under gentle reflux, filtered, and the product was isolated from the filtrate by evaporation of ether. Phenyllithium was determined after drying overnight under vacuum by titrating an aqueous tetrahydrofuran (hereafter abbreviated THF) solution of the solid with standardized hydrochloric acid.

The phenyllithium was used to make the aryl metal complex, $Li(THF)_4Ta(C_6H_5)_6$, the tantalum source, as follows:

To 52 g. (0.15 moles) of $TaCl_5$ in a stirred mixture of 1400 ml. of benzene and 50 ml. of diethyl ether at 5° was added over a 1 hr. period 0.73 moles of $C_6H_5Li$ prepared as described above. The mixture was stirred for one hour at room temperature. The solution was filtered and to the filtrate was added 200 ml. of THF. After 10 minutes, orange, crystalline $Li(THF)_4Ta(C_6H_5)_6$ precipitated from solution. It was isolated by filtration and washed with ether.

The $Li(THF)_4Ta(C_6H_5)_6$, (9.0 g.; 9.6 mmole), was mixed with 4.5 g. (30 mmole) of $(CH_3)_2PCH_2CH_2P(CH_3)_2$, hereafter called dmpe, and 40 ml. of sodium-dried THF in a 100 ml. stainless steel pressure vessel (bomb). The dmpe was prepared by the method of G. W. Parshall J. Inorg. and Nucl. Chem. 14, 291 (1960), wherein it was called tetramethylethylenediphosphine. The vessel was chilled, evacuated, and pressured with hydrogen. The temperature was then raised to 80°, the pressure adjusted to 200 atm, and the vessel shaken for 5 hours. The vessel was allowed to stand at room temperature under pressure overnight. Pressure was then released and the bomb opened. The reaction mixture contained a liquid phase, A, and an orange solid phase, B. The phases were separated by filtration. Solvent and excess dmpe were evaporated under vacuum from the liquid phase to yield a brown solid. This solid was extracted with n-hexane, previously dried over a 4A molecular sieve. The soluble portion was crystallized from n-hexane to yield 1.3 g. of tan crystalline solid.

Treatment of the tan product was degassed activated charcoal in n-hexane solution, followed by recrystallization yielded off-white $[(CH_3)_2PCH_2CH_2P(CH_3)_2]_2TaH_5$, of melting point 133° to 135°.

Anal. Calcd. for $[(CH_3)_2PCH_2CH_2P(CH_3)_2]_2TaH_5$:

C, 29.6; H, 7.7; P, 25.5; Ta, 37.2 Found: C, 29.8; H, 7.8; P, 25.5; Ta, 37.5; IR 1550 cm$^{-1}$ (Ta-H stretching frequency); $^1$Hnmr ($C_6D_6$ solution, 220 MH$_z$) $\tau 8.58 - \tau 8.67$ (area 32 $(CH_3)_2PCH_2CH_2P(CH_3)_2$; $\tau 10.82$ (quintet, area 5, $J_{PH} = 32.3$ Hz, Ta-H); $^{31}$Pnmr, sextet ($J_{PH} = 32.3$ Hz).

Taken together, the $^{31}$p and $^1$H nmr data show that there are 5 metal hydride ligands and 2 $(CH_3)_2PCH_2CH_2P(CH_3)_2$ ligands per Ta.

An additional quantity of $(dmpe)_2TaH_5$ can be obtained from the solid phase, B, initially recovered from the reaction vessel by treating said solid with a small amount of ethanol in benzene. About 20% ethanol by weight of the solid is sufficient; excess alcohol should be avoided. After evaporation of the solvent, the $(dmpe)_2TaH_5$ can be further purfied by recrystallization from n-hexane.

$[(CH_3)_2PCH_2CH_2P(CH_3)_2]_2NbH_5$

The corresponding niobium compound, $(dmpe)_2NbH_5$, can be similarly prepared by following the procedure of this Example but using as a metal source the known aryl compound, $(C_6H_5)_4Nb \cdot 2LiC_6H_5$.

EXAMPLE 2

Preparation of [(CH$_3$)$_2$PCH$_2$CH$_2$P(CH$_3$)$_2$]$_2$TaH$_5$

TaCl$_5$, 1.8 g. (5.0 mmole), was mixed with 3.8 g. (25 mmole) of dmpe, 10 ml. of sodium-dried benzene and 2.0 g. of (51 mmole) of potassium metal in a 100 ml. Hastelloy C pressure vessel. The vessel, pressured to 200 atm. with hydrogen, was shaken overnight at 115°. The reaction mixture was filtered and the product isolated by evaporation of solvent from the filtrate. After recrystallization from n-hexane 0.45 g. of (dmpe)$_2$TaH$_5$ was obtained. The properties of this compound were identical with those of the compound prepared by the method of Example 1.

Using exactly the same procedure with NbCl$_5$ as the metal source, the corresponding niobium compound can be prepared.

The novel pentahydrido complexes can be used as intermediates to form the lower hydrides of Nb and Ta by treating them with the additional quantities of the desired ligand, preferably the more stable chelate ligands, in an atmosphere of controlled low hydrogen pressure.

EXAMPLE 3

Preparation of [(CH$_3$)$_3$P]$_4$TaH$_5$

Using the method of Example 1, 1.0 g. of Li(THF)$_4$-Ta(C$_6$H$_5$)$_6$ was mixed with 2 ml. of (CH$_3$)$_3$P and 2 ml. of benzene in a 10 ml. stainless steel pressure vessel. The reagents were agitated under 200 atm. hydrogen pressure for 2 hours at 50° and then overnight at room temperature. The mixture was filtered and solvent evaporated from the filtrate to yield a brown solid. The Ta-H stretching frequency at 1565 cm$^{-1}$ and the $^1$H nmr spectrum $\tau$8.57, (CH$_3$P); $\tau$9.07 (quintet, J = 40 Hz, TaH) characterize the product as [(CH$_3$)$_3$P]$_4$TaH$_5$.

EXAMPLE 4

Preparation of (CH$_3$)$_2$PCH$_2$CH$_2$P(CH$_3$)$_2$ZrH$_3$

Tetrabenzylzirconium was used as a source of zirconium. It was prepared by the Grignard method of Zucchini et al., J. Organometal. Chem., 26, 357–372 (1971), using benzylmagnesium chloride and ZrCl$_4$. Tetrabenzylzirconium, 13.7 g. (30 mmole), dmpe, 11.2 g. (75 mmole) and 50 ml. of benzene were added to a 100 ml. stainless steel pressure vessel. The contents of the vessel were agitated overnight at room temperature under 200 atm. of hydrogen. The reaction mixture was filtered to remove solid impurities. Solvent and excess dmpe were removed from the filtrate under vacuum. The resulting dark brown solid was dissolved in toluene and precipitated from this solution by addition of n-hexane. The solid was dried under vacuum to yield 2.5 g. of dark brown product.

Anal. Calcd. for (CH$_3$)$_2$PCH$_2$CH$_2$P(CH$_3$)$_2$ZrH$_3$: C, 29.5; H, 7.8; P, 25.4; Zr, 37.3 Found: C, 32.9; H, 7.9; P, 23.2; Zr, 37.2 IR: 1280 cm$^{-1}$ (broad, intense Zr-H-Zr vibration).

These data show the compound to contain dmpe and Zr in a 1:1 ratio, and that Zr-H-Zr units are present. The number of hydrogens attached to the metal were determined by reacting the complex with hydrogen chloride and measuring the evolved hydrogen gas. A 0.2615 g. (1.07 mmole) sample of the compound were dissolved in 15 ml. of toluene and treated with 7 mmole of hydrogen chloride. Hydrogen gas, 3.37 mmole, was rapidly evolved. The amount of this gas corresponds to the presence of 3 hydride ligands/Zr atom. The empirical formula of the compound is thus determined to be (CH$_3$)$_2$PCH$_2$CH$_2$P(CH$_3$)$_2$ZrH$_3$.

EXAMPLE 5

Preparation of (CH$_3$)$_2$P(CH$_2$)$_2$P(CH$_3$)$_2$TiH$_3$

Tetrabenzyltitanium was prepared by the Grignard method of Zucchini et al., J. Organometal. Chem., 26, 357–372 (1971) using benzylmagnesium chloride and TiCl$_4$. Its reaction with dmpe and hydrogen was conducted using the procedure described in Example 4 for the preparation of (dmpe)ZrH$_3$. The product was isolated by removal of solvent and excess dmpe from the filterd reaction mixture under vacuum. The black solid obtained was washed with n-hexane, dried, and analzyed.

Anal. Calcd. for (CH$_3$)$_2$PCH$_2$CH$_2$P(CH$_3$)$_2$TiH$_3$: C, 35.8; H, 9.5; Ti, 23.8. Found: C, 35.9; H, 7.7; Ti, 24.0.

EXAMPLE 6

Preparation of (CH$_3$)$_2$PCH$_2$CH$_2$P(CH$_3$)$_2$HfH$_3$

Tetrabenzylhafnium was prepared by the following procedure: Toluene, 130 ml., was added to 0.2 moles of benzylmagnesium chloride in ether solution. The ether was removed under vacuum and an additional 150 ml. of toluene was added to the gelatinous mixture and, with stirring, 14 g. (0.044 mole) of HfCl$_4$ was added in portions. The temperature was maintained below 30° by external cooling. After the addition was complete, the mixture was further stirred for 2 hours. Solids were centifuged off and the product isolated from the solution by removal of solvent under vacuum. The yellow product after washing with n-hexane weighed 9.9 g.

This material was recrystallized from a mixture of 80% toluene and 20% n-hexane at −25° to yield yellow crystalline (C$_6$H$_5$CH$_2$)$_4$Hf, mp 109°-110°.

Tetrabenzylhafnium, 0.54 g. (1.0 mmole), dmpe, 0.30 g. (2.0 mmole) and benzene, 3.5 ml., were mixed in a 10 ml. stainless steel pressure vessel. The mixture was agitated and heated at 90° for 5 hours under 400 atm. of hydrogen. Solvent was removed from the soluble fraction to yield a tan solid. The infrared spectrum of the solid contained an intense broad band at 1300 cm$^{-1}$ which shows the compound to be (CH$_3$)$_2$PCH$_2$CH$_2$P(CH$_3$)$_2$HfH$_3$.

EXAMPLE 7

Preparation of [(CH$_3$)$_2$PCH$_2$CH$_2$P(CH$_3$)$_2$]P(CH$_3$)$_3$NbH$_3$ 0.398 g. (1 mmole) of [Me$_2$PCH$_2$CH$_2$PMe$_2$]$_2$NbH$_5$ (prepared in Example 1) was dissolved in hexane and stirred with one mmole of PMe$_3$ overnight to give an orange solution and 1.03 mmoles of gas not condensable by liquid nitrogen which was assumed to be hydrogen. Removal of the solvent left 450 mg. of (PMe$_3$)-[Me$_2$PCH$_2$CH$_2$PMe$_2$]$_2$NbH$_3$ as an orange solid.

The infrared spectrum showed the metal-hydride absorption at ca. 1560 cm.$^{-1}$.

EXAMPLE 8

Preparation of [(CH$_3$)$_2$PCH$_2$CH$_2$P(CH$_3$)$_2$]$_3$NbH 0.398 g. (1 mmole) of [Me$_2$PCH$_2$CH$_2$PMe$_2$]$_2$NbH$_5$ (prepared in Example 1) and 150 mg. of Me$_2$PCH$_2$CH$_2$PMe$_2$ were refluxed in 50 ml. of hexane for 48 hours.

Filtration gave .35 g. of [Me$_2$PCH$_2$CH$_2$PMe$_2$]$_3$NbH as large red octahedral crystals.

A sample prepared by an essentially identical procedure was analyzed. Calc. for NbC$_{18}$H$_{40}$P$_6$: C, 39.78; H, 8.92. Found: C, 39.63, 39.59, 39.33; H, 8.94, 9.01, 8.98.

UTILITY

All of the complex hydrides of the invention are useful as reducing agents for the formation of metals such as Ag from their salts. They are particularly useful for the hydrogenation of olefins. As catalysts for olefin polymerization, they have been found to form dimers as well as polymers.

A. Reduction of Silver Ion with (dmpe)$_2$TaH$_5$.

A solution of (dmpe)$_2$TaH$_5$ in acetonitrile was added to an acetonitrile solution of silver nitrate. After 1 minute at room temperature, a silver mirror formed on the walls of the glass reaction vessel.

B. Reduction of Silver Ion with (dmpe)ZrH$_3$.

A solution of (dmpe)ZrH$_3$ in benzene was added to an acetonitrile solution of silver nitrate. On mixing, a silver mirror formed on the walls of the glass reaction vessel.

C. Hydrogenation and Dimerization of Ethylene by (dmpe)$_2$-TaH$_5$.

A 10 ml. stainless steel pressure vessel was charged with 0.05 g. of (dmpe)$_2$TaH$_5$ and 3 ml. of C$_6$H$_6$. Ethylene, 50 atm., and hydrogen, 250 atm., were added at room temperature. The mixture was heated at 80° for 3 hours. Analysis of the gaseous product mixture showed ethane, butane, and ethylene to be present in a ratio of 92.8: 1.4:5.8, respectively.

D. Hydrogenation and Dimerization of Ethylene by (dmpe)ZrH$_3$.

A 10 ml. stainless steel pressure vessel was charged with 0.05 g. of (dmpe)ZrH$_3$ and 3 ml. of C$_6$H$_6$. The gaseous reagents and conditions were like those described in C. The gaseous product consisted primarily of ethane and butane.

E. Hydrogenation, Dimerization and Polymerization of Ethylene by (dmpe)TiH$_3$.

Three-tenths of a gram of (dmpe)TiH$_3$ and 3 ml. of benzene were mixed in a 10 ml. stainless steel pressure vessel. Ethylene, 100 atm, was added and the mixture agitated overnight at room temperature. The reaction products consisted of polyethylene, ethane and butane.

Although the invention has been described and exemplified by way of specific embodiments, it is not intended that it be limited thereto. As will be apparent to those skilled in the art, numerous modifications and variations of these embodiments can be made without departing from the spirit of the invention or the scope of the following claims.

The embodiments of the invention in which an exclusive property or privilege is claimed are defined as follows:

1. Hydrides of the formula
   wherein:
   M is Nb, Ta, Ti, Zr, or Hf
   R is alkyl, aryl, alkaryl or aralkyl of up to 8 carbon atoms
   R' is alkyl, aryl, alkaryl or aralkyl of up to 8 carbon atoms
   R'' is alkylene of up to 3 carbon atoms, or o-phenylene
   with the provisos that: when
   M is Nb or Ta,
   $x = 0, 1, 2$ or $4$; $y = 0, 2$ or $3$; $z = 1, 3$ or $5$; and $2x + 4y + z = 13$; and
   when,
   M is Ti, Zr of Hf,
   $x = 0, y = 1$, and $z = 3$.

2. A hydride according to claim 1, wherein
   R is methyl, ethyl or phenyl,
   R' is methyl or phenyl, and
   R'' is —CH$_2$CH$_2$— or o-phenylene.

3. A hydride according to claim 2, wherein M is Nb or Ta.

4. A hydride according to claim 3, where $x = 0$, of the formula (R'$_2$PR''PR'$_2$)$_2$MH$_5$.

5. A hydride according to claim 4, [(CH$_3$)$_2$PCH$_2$CH$_2$P(CH$_3$)$_2$]$_2$NbH$_5$.

6. A hydride according to claim 4, [(CH$_3$)$_2$PCH$_2$CH$_2$P(CH$_3$)$_2$]$_2$TaH$_5$.

7. A hydride according to claim 3, where $y = 0$, of the formula
   (PR$_3$)$_4$MH$_5$
   wherein R is methyl, ethyl or phenyl.

8. A hydride according to claim 7 of the formula ](CH$_3$)$_3$P]$_4$TaH$_5$.

9. A hydride according to claim 3 of the formula (PR$_3$) (R'$_2$PR''PR'$_2$)$_2$MH$_3$.

10. A hydride according to claim 9 of the formula P(CH$_3$)$_3$[(CH$_3$)$_2$PCH$_2$CH$_2$P(CH$_3$)$_2$]$_2$NbH$_3$.

11. A hydride according to claim 3, where $x = 0$, of the formula (R'$_2$PR''PR'$_2$)$_3$NbH.

12. A hydride according to claim 11 of the formula [(CH$_3$)$_2$PCH$_2$CH$_2$P(CH$_3$)$_2$]$_3$NbH.

13. A hydride according to claim 1, wherein M is Ti, Zr or Hf.

14. A hydride according to claim 13, wherein
    R is methyl, ethyl or phenyl,
    R' is methyl or phenyl, and
    R'' is —CH$_2$CH$_2$— or o-phenylene 15. A hydride according to claim 14 of the formula R'$_2$PR''PR'$_2$MH$_3$.

16. A hydride according to claim 15 of the formula (CH$_3$)$_2$PCH$_2$CH$_2$P(CH$_3$)$_2$TiH$_3$.

17. A hydride according to claim 15 of the formula (CH$_3$)$_2$PCH$_2$CH$_2$P(CH$_3$)$_2$ZrH$_3$.

18. A hydride according to claim 15 of the formula (CH$_3$)$_2$PCH$_2$CH$_2$P(CH$_3$)$_2$HfH$_3$.

19. The process for making a hydride of claim 1 comprising reacting
    a metal-source compound selected from the group consisting of metal alkyls, aryls, alkaryls and aralkyls with
    a tertiary phosphine selected from the group consisting of PR$_3$ and R$_2$'PCH$_2$CH$_2$PR'$_2$ in the presence of a source of hydrogen.

20. The process of claim 19 wherein the source of hydrogen is hydrogen gas.

21. The process of claim 19 wherein the metal-source compound is a phenyl compound of the metal.

22. The process of claim 19 wherein the metal-source compound is a benzyl compound of the metal.

* * * * *